US010139423B2

(12) United States Patent
Brisebat et al.

(10) Patent No.: US 10,139,423 B2
(45) Date of Patent: Nov. 27, 2018

(54) MEDICAL ANALYSIS METHOD

(71) Applicants: BIO-RAD INNOVATIONS, Marnes la Coquette (FR); DiaMed GmbH, Cressier (CH)

(72) Inventors: Jean-Michel Brisebat, Villers (FR); Sébastien Bernay, Ecoche (FR); Cédric Gagnepain, Riorges (FR); Daniel Seydoux, Le Mesnil Saint Denis (FR)

(73) Assignees: BIO-RAD INNOVATIONS, Marnes la Coquette (FR); DiaMed GmbH, Cressier (CH)

( * ) Notice: Subject to any disclaimer, the term of this patent is extended or adjusted under 35 U.S.C. 154(b) by 0 days.

(21) Appl. No.: 14/383,749

(22) PCT Filed: Mar. 8, 2013

(86) PCT No.: PCT/FR2013/050489
§ 371 (c)(1),
(2) Date: Sep. 8, 2014

(87) PCT Pub. No.: WO2013/132195
PCT Pub. Date: Sep. 12, 2013

(65) Prior Publication Data
US 2015/0111198 A1    Apr. 23, 2015

(30) Foreign Application Priority Data

Mar. 8, 2012 (FR) ...................................... 12 52116

(51) Int. Cl.
*G01N 35/04* (2006.01)
*G01N 35/10* (2006.01)
*G01N 35/00* (2006.01)

(52) U.S. Cl.
CPC ..... *G01N 35/0099* (2013.01); *G01N 35/1081* (2013.01); *G01N 35/109* (2013.01); *Y10S 901/31* (2013.01); *Y10T 436/114165* (2015.01)

(58) Field of Classification Search
CPC .................................................. G01N 35/0099
See application file for complete search history.

(56) References Cited

U.S. PATENT DOCUMENTS

| 6,060,022 A | 5/2000 | Pang et al. |
| 7,174,830 B1 | 2/2007 | Dong |
| (Continued) | | |

FOREIGN PATENT DOCUMENTS

| EP | 2458387 A2 | 5/2012 |
| JP | 2003130184 | 5/2003 |
| (Continued) | | |

OTHER PUBLICATIONS

English Translation of Office Action from Japanese Patent Application No. 2014-560434, dated Nov. 15, 2016, 11 pages.

*Primary Examiner* — Kathryn Wright
(74) *Attorney, Agent, or Firm* — Lee & Hayes, PC

(57) ABSTRACT

A medical analysis method uses a medical analysis machine provided with a poly-articulated robot (70) comprising joints defining at least six axes of rotation (A1, A2, A3, A4, A5, A6) and adapted for spacing and/or orienting a terminal member (66) according to six degrees of freedom, the terminal member bearing a grasping member (78) adapted for grasping a container (16). The medical analysis method comprises at least the succession of steps consisting of providing a container (16) containing a sample to be treated stemming from a human being or an animal, transferring said container (16) towards at least one treatment station of the medical analysis machine (100) by means of the poly-articulated robot, treating the sample in a treatment station, (Continued)

transferring the container towards a station for capturing images, and displaying the treatment results through a user interface.

13 Claims, 4 Drawing Sheets

(56) References Cited

U.S. PATENT DOCUMENTS

| | | | |
|---|---|---|---|
| 2008/0206855 A1 | 8/2008 | Sipes et al. | |
| 2009/0302795 A1* | 12/2009 | Nichols | B25J 13/086 |
| | | | 318/568.13 |
| 2010/0015726 A1* | 1/2010 | Jakubowicz | B01J 19/0046 |
| | | | 436/518 |
| 2010/0288060 A1* | 11/2010 | Ronsick | G01N 35/0099 |
| | | | 73/864.63 |
| 2012/0134896 A1* | 5/2012 | Chiyajo | G01N 35/0099 |
| | | | 422/549 |

FOREIGN PATENT DOCUMENTS

| | | |
|---|---|---|
| JP | 2005181135 | 7/2005 |
| JP | 2008304467 | 12/2008 |
| JP | 2010025939 | 2/2010 |

\* cited by examiner

MEDICAL ANALYSIS METHOD

CROSS-REFERENCE TO RELATED APPLICATIONS

This Application is the National Stage of International Application No. PCT/FR2013/050489, filed Mar. 8, 2013, which claims priority to French Patent Application No. 1252116, filed Mar. 8, 2012, the entire disclosures of which are incorporated herein by reference.

The present invention relates to the field of medical analysis.

More particularly, it relates to a method for medical analysis.

In the present disclosure, by "medical analysis" is meant a process consisting of treating at least one sample from a human being or from an animal. Such samples are for example samples of body fluid (blood, urine, lymph, saliva, etc.), cells, biological or organ tissues.

Examples of medical analyses are immuno-hematology analyses such as blood group tests, tests for searching for antibodies such as irregular agglutinins, or tests for determining compatibility between a donor and a receiver (cross-matched tests).

The present disclosure more particularly relates to a medical analysis method in vitro.

Presently, medical analysis methods are achieved by means of apparatuses, also called analysis machines, which allow automation of certain operations which would otherwise be dealt with manually by one or several users within medical analysis laboratories, for example, the loading into a centrifuge of analysis containers containing blood samples or any other sample.

Such machines, used in medical analysis methods, are for example known from documents U.S. Pat. No. 6,162,399, JP 2010054232 and EP 2145685. These machines all use robots of the Cartesian type.

These machines, using Cartesian robots, are therefore generally limited to the handling of a limited number of particular treatment stations.

Their dimensions therefore inevitably increase as soon as it is desired to multiply the number of their workstations. Now, the available surface area for installing machines is increasingly limited because of the densification of services within existing analysis laboratories.

Moreover, the robots of the Cartesian type have the particularity of simplifying the modelling of the workspace by only taking into account the position of the objects in space, independently of their orientation. The reducing nature of this approach assumes that the orientation of the objects to be managed is known in advance, set and reproducible on a large number of machines produced in series. The mounting of the machine should therefore be ensured with a high degree of accuracy.

The goal of the present invention is to provide a medical analysis method in which repetitive gestures of the users, which are time consuming and source of error, are automated to a maximum, while requiring only a limited workspace.

This object is achieved with a medical analysis method using a medical analysis machine provided with a poly-articulated robot comprising joints defining at least six axis of rotation and adapted for displacing and/or orienting a terminal member according to six degrees of freedom, the terminal member bearing a grasping member suitable for grasping a container, said medical analysis method comprising at least the succession of the following steps:

a container is provided, filled beforehand with a sample to be treated stemming from a human being or an animal, said container is transferred towards at least one treatment station of the medical analysis machine by means of the poly-articulated robot, the sample is treated in the treatment station, the container is transferred to a station for capturing images and the results of the treatment are displayed on a user interface.

In other words, the invention relates to the use in a medical analysis machine of a poly-articulated robot comprising joints defining at least six axis of rotation and adapted for displacing and/or orienting a terminal member according to six degrees of freedom, the terminal member bearing a grasping member adapted for grasping a container, the medical analysis machine being adapted to the application of the medical analysis method comprising at least the steps consisting of providing a container filled beforehand with a sample to be treated stemming from a human being or an animal, transferring the container towards at least one treatment station of the medical analysis machine by means of the poly-articulated robot, treating the sample in the treatment station, and transferring the container towards a station for capturing images and then displaying the results of treatment on a user interface.

In the present disclosure, by treatment station is meant any station in which the container, and more particularly the sample which it contains, is treated. By treating is generally meant any action intended to view or control the container, or to introduce therein a substance, notably a reagent, or further to modify the physical properties (temperature, homogeneity, etc) of the contents of the container.

During the treatment step, the container may thus for example be brought into a pipetting area so as to introduce therein a reagent, into an incubator in order to be incubated, into a centrifuge in order to be centrifuged, etc.

Moreover, in the present disclosure, a station for capturing images should be understood as any device allowing an image to be taken, such as a photographic image for example of the container, and notably of the treated sample. The station for capturing images of the treatment results may notably comprise a camera for capturing images.

Finally, the user interface should be understood as any device with which an operator may interact and which comprises a display member such as a screen. The user interface may not be part of the medical analysis machine. The images of the treated container captured by the station for capturing images are sent to the user interface so as to allow viewing of the container, and in particular of the sample, or of reaction results which are interpreted by a software package on the basis of the captured images.

According to an embodiment of the invention, the treatment of the sample comprises the introduction into the container of a reagent adapted to react with the sample to be treated.

When the reagent is introduced into the container and is put into contact and optionally mixed with the sample to be treated, a reaction occurs between the sample and the reagent, said reaction may be positive or negative.

The station for capturing images then captures images of the results of the reaction conducted in the container between the sample to be treated and the reagent introduced into the container. The captured images may therefore be witnesses of a so-called "positive" reaction or of a so-called "negative" reaction. These captured images or results inferred from the interpretation of these images by a software package are, as previously, displayed on the display device of the user interface. In particular, these captured images or the reaction results inferred from the interpretation of these images by a software package may be witnesses of the reaction degree between the sample and the reagent.

In certain embodiments, steps are carried out by means of the poly-articulated robot, upstream from the steps for providing and treating the container containing the sample, for example, the method may comprise a prior step during which the sample is extracted from a storage container, notably a tube, and introduced into the container, by means of the poly-articulated robot.

The method may also comprise steps for treating the container before the sample is introduced therein, notably identifying the container by viewing an identifier of said container, such as a printed bar code for example, capturing the dimensions of the container, etc.

In certain embodiments, the method comprises a step for analysis, notably automatic analysis, of the displayed treatment results. The method may notably comprise a step for interpretation intended to provide a piece of information, notably on the physiological or pathological condition of a person or on a congenital abnormality.

For example, the station for capturing images of the results of the treatment of the sample may be coupled with a software package suitable for analysis of the treatment results. Such a software package may notably be set up on a computer of the user interface.

For the case when the step for treating the sample comprises the introduction of a reagent into the container, the analysis of the reaction results by the software package for example, may notably allow an automatic conclusion as to the positivity or negativity of the reaction.

The medical analysis method according to the invention, particularly finds its application in immuno-hematology, for example in blood group tests, tests for searching for antibodies such as irregular agglutinins or for determining compatibility between a donor and a receiver.

Other fields in which the method according to invention may be applied are biology, microbiology, bacteriology, mycology, parasitology, quality control for a laboratory for diagnostic in vitro, detection of auto-immune diseases, monitoring diabetes, detecting genetic diseases, toxicology and the monitoring of a physiological or pathological condition, notably as a result of therapeutic treatment.

Preferably, in the method according to the invention a poly-articulated robot secured to a fixed base and which exclusively comprises rotoidal joints is used.

The container grasped and displaced by the poly-articulated robot may for example be a gel card. Typically, a gel card is a container including a body in which are formed several adjacent reaction wells positioned along a single row and obturated by a lid. The wells of the gel card generally contain a gel used for interpretation of the reaction results having occurred in the wells. For example, the body of the gel card is in plastic. Further, generally, a gel card comprises 6 to 8 wells. It is then understood that the sample to be tested is introduced into at least one well of such a gel card.

In the cases when a reagent has to interact with the sample to be treated, the reagent may be introduced into at least one well of the gel card. The reagent may for example be a suspension of test erythrocytes dispensed in the container comprising a plasma to be tested or a test serum dispensed in the container containing a suspension of erythrocytes to be tested.

According to an embodiment of the method according to the invention, the container is brought to the station for capturing an image of the treatment results by means of the poly-articulated robot.

In this case, the station for capturing images of the treatment results is integrated to the medical analysis machine. It is understood that these captured images are then sent to the user interface for displaying these images.

According to an embodiment, prior to the steps for displaying the treatment results, the container or another receptacle is brought by means of the poly-articulated robot to a control station connected to the user interface.

In the present disclosure, a control station should be understood as any device allowing capture of images intended for allowing control of the container and being part of the medical analysis machine.

By control, is for example meant the identification of the container, notably of an identifier of the container, such as a printed barcode on the latter for example, the control of the level of the liquids in the container, the capture of the dimensions of the container, notably its height and its diameter, the control of the condition of the air gaps i.e. air bubbles isolating the liquid(s) dispensed in the container, or further the control of the quality of the contents of the container, notably of a gel. The control station may also capture images of objects manipulated by the poly-articulated robot, other than the container. For example, it may allow determination of a liquid level in a reagent flask.

In certain embodiments, the station for capturing images of the results of the treatment and the control station are a single and same station, connected to the user interface for displaying the results of the treatment, i.e. captured images or results resulting from the interpretation of these images by a software package.

According to an example, the control station comprises a camera. The captured control images are then displayed on the user interface or a message relating to these images is displayed on the user interface.

In certain embodiments, the container is brought by means of the poly-articulated robot up to a centrifuge of the medical analysis machine.

In certain embodiments, the container is brought by means of the poly-articulated robot as far as an incubator of the medical analysis machine.

In certain embodiments, the container is displaced by means of the poly-articulated robot to an area for pipetting the container of the medical analysis machine in order to introduce a reagent therein.

In certain embodiments, the grasping member of the poly-articulated robot is used for grasping a reagent flask.

In certain embodiments, the reagent flask is displaced by means of the robot to an area for pipetting the reagent.

In certain embodiments, the reagent flask may be turned upside down and/or stirred by means of the poly-articulated robot in order to re-suspend it.

In certain embodiments, the poly-articulated robot adjusts the sharpness of a camera of the control station and/or of the station for capturing images of the results of the treatment.

In certain embodiments, the poly-articulated robot pivots the container by an angle of 180°, in order to take a picture of each face of the container.

In certain embodiments, the machine comprises a plurality of treatment stations which are distributed over 360° around the poly-articulated robot.

In certain embodiments, the poly-articulated robot has access to each treatment station of the machine.

In certain embodiments, the container is displaced by means of the poly-articulated robot to a collecting container intended for recovering waste.

In certain embodiments, the method comprises a prior parameterization step during which areas where the poly-articulated robot is allowed to move and areas into which the robot cannot penetrate are predefined, notably in order to prevent overflying of certain areas of the medical analysis machine. This functionality is particularly important for reducing cross-contamination risks upon manipulating different samples, diluents, and/or reagents.

In certain embodiments, the terminal member of the robot comprises a piezo-electric touch probe.

In certain embodiments, the sample comprises one of the substances selected from a fluid, a cell, a biological or organ tissue stemming from a human being or an animal.

In a particular embodiment, the method comprises the following steps:
  the container filled beforehand with the sample to be treated by means of the poly-articulated robot is brought towards a pipetting area of said container in order to introduce a reagent therein,
  the reagent is introduced into the container,
  the container is brought back to an incubator by means of the poly-articulated robot,
  the container is incubated,
  the container is brought by means of the poly-articulated robot from the incubator to a centrifuge,
  the container is centrifuged,
  the container is transferred to the station for capturing images of the treatment reactions and the results are displayed by the user interface.

In certain embodiments, before the step of introducing the reagent into the container, the flask of reagent is turned upside down and/or stirred by means of the poly-articulated robot, the reagent being thereby re-suspended.

In certain embodiments, prior to the centrifugation step, the container is transferred by means of a poly-articulated robot to the control station in order to check the air-gaps.

In certain embodiments, the poly-articulated robot is used for actuating an element of the medical analysis machine.

In certain embodiments, the orientation of the poly-articulated robot is controlled depending on the nature of the object to be displaced, notably in order to avoid overflows or stirring of the liquid in the case when the robot displaces a container filled with liquid.

In certain embodiments, the speed of the poly-articulated robot is controlled according to the nature of the object to be displaced, notably for avoiding overflows or stirring of the liquid in the case when the robot displaces a container filled with liquid.

In certain embodiments, the force applied by the grasping member on the object to be displaced is measured.

In certain embodiments, the poly-articulated robot is used for stirring an object (for example a container with a diluent), notably for re-suspending or mixing the liquid in the case where the object is a container filled with liquid.

The invention also relates to a medical analysis machine which may be used for applying the method defined above, notably an in vitro medical analysis machine, for example in immuno-hematology, comprising a poly-articulated robot comprising joints defining at least six axes of rotation and adapted for displacing and/or orienting a terminal member according to six degrees of freedom.

The medical analysis machine according to the invention comprises, in addition to such a poly-articulated robot, storage and/or analysis members notably allowing the storage of containers (sample tubes, diluent container, reagent container, etc) and/or the capture of images, notably of a treatment result.

The robot used in the present invention is poly-articulated like a human arm, and comprises six degrees of freedom (three degrees of freedom for displacement and three degrees of freedom for orientation), allowing displacement and orientation of the distal end of the arm or terminal member, in a given workspace.

It thus covers a work area (i.e. an area for the motion of the terminal member) which may be approximately symbolized by a sphere, the robot being placed at the center of this sphere. By means of the six degrees of freedom of the terminal member, not only the actual position of the constitutive elements of the machine and of the receptacles handled by the latter may be taken into account, but still their orientation in space. The terminal member of the robot may therefore attain workstations located in any location around the base of the robot, in all the directions of space.

The compactness of the workspace of the machine may thus be increased, the work stations may be brought closer to each other.

With prior learning of the workspace and by storing in memory the real spatial coordinates of each object, the poly-articulated robot has a true non-virtual image of the machine, allowing compensation for the geometry defects due to building inaccuracies.

In a preferred embodiment of the invention, the poly-articulated robot is secured to a fixed base and exclusively comprises rotoidal joints. Thus the displacements of the robot are exclusively ensured by pivot joints.

In certain embodiments, a container is displaced by means of the poly-articulated robot to an outlet magazine of the containers. This handling is notably useful when it is desired to recover the container for controlling it or else for reusing it subsequently (for example when the container is a gel card and that all the wells of said gel card have not been treated).

Several embodiments or applications are described in the present disclosure. However, unless specified otherwise, the characteristics described in connection with any embodiment may be applied to another embodiment or application.

Other features and advantages of the invention will become apparent upon reading the following description of exemplary embodiments of the invention given as an illustration and not as a limitation. This description refers to the appended sheets of drawings wherein:

FIG. 1 illustrates a medical analysis machine, adapted for testing blood samples.

Figure 1:
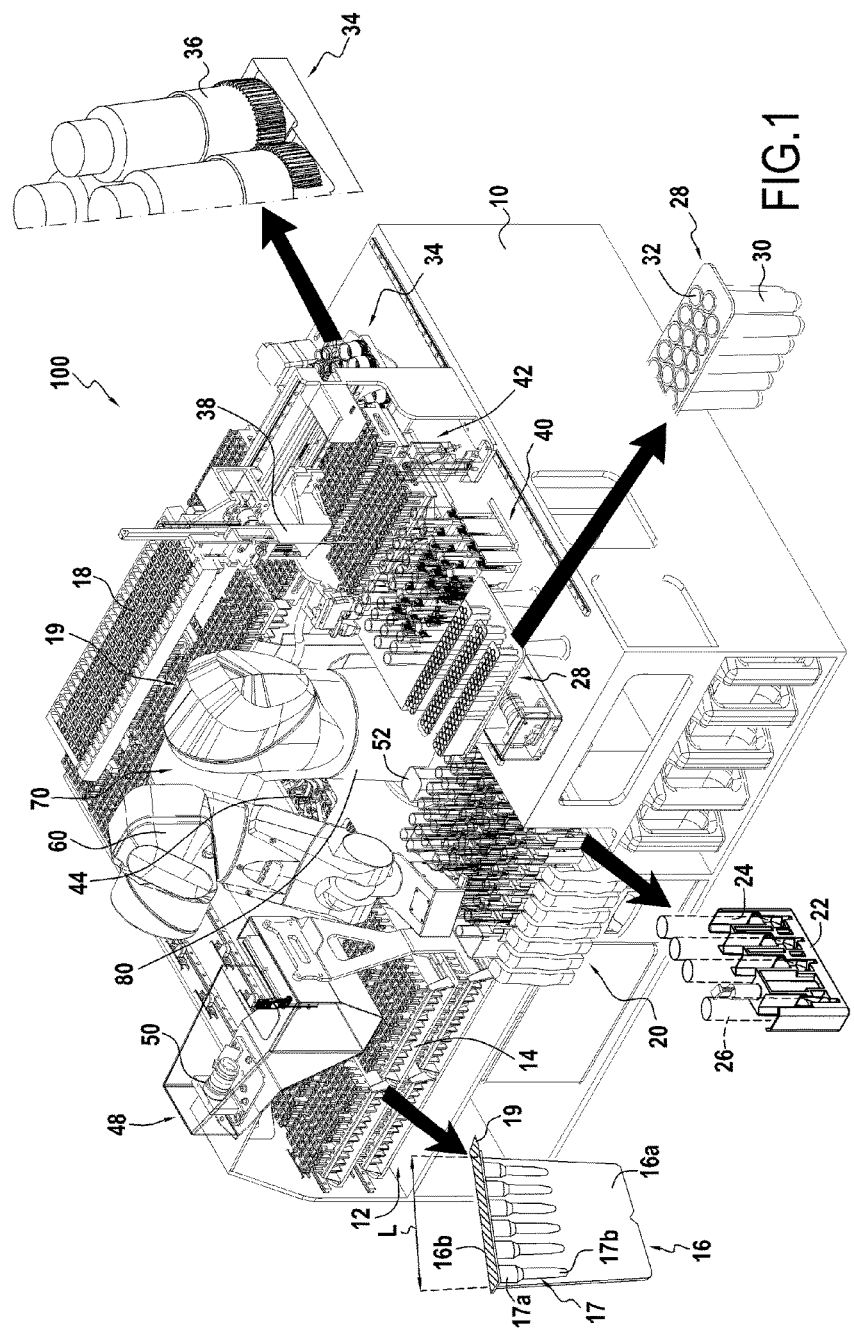
FIG. 1 is a perspective view of an exemplary machine capable of treating clinical samples for analysis in immuno-hematology.

In the example, the analysis carried out by means of this machine aims at detecting a reaction between antigens (a substance capable of triggering an immune reaction) and antibodies (protein of the blood serum secreted by white corpuscles involved in immunity in the presence of an antigen) by agglutination.

This analysis finds its application notably in phenotyping tests of a blood group, for searching antibodies such as irregular agglutinins, and for determining compatibility between a donor and a receiver.

It may be carried out in two ways. Either it is intended for seeking the presence or the absence of antigens at the surface of erythrocytes and in this case, a test serum with a known composition of antibodies is put into the presence of erythrocytes of a patient to be tested, or it is intended for seeking the presence or the absence of particular antibodies in a given sample and in this case the sample to be tested which is generally the serum or the plasma of the patient is put into the presence of test erythrocytes.

In both cases however, the principle on which is based the analysis remains the same.

A suspension of erythrocytes (test erythrocytes or those to be tested) is taken from a sample tube by means of a pipette. This suspension is optionally obtained beforehand by introducing erythrocytes into a diluent such as saline or any other suitable diluent.

The suspension of erythrocytes is then introduced into a container, notably a tube, containing a gel. In the example, the suspension is introduced into a gel card well, a gel card being typically a card provided with a plurality of wells (generally six or eight) containing a gel and initially obturated by a cover.

A reagent solution comprising antibodies, notably depending on the case, the plasma of a patient or a test serum is pipetted into a reagent flask and in turn introduced into the well of the gel card.

After having been optionally incubated, the gel card is introduced into a centrifuge and centrifuged.

The reaction is considered as positive when a specific bond is generated between the antibodies of the plasma or serum and the surface antigens of the erythrocytes, and that they form an agglutinate of particles.

Under the effect of centrifugation, in the absence of any agglutinate (i.e. in the case of a negative reaction), the erythrocytes pass through the gel contained in the well of the gel card and concentrate at the bottom of the well.

In the presence of agglutinates (i.e. in the case of a positive reaction), on the other hand, the erythrocytes remain at the surface of the gel during centrifugation.

In order to allow the user to view the reaction results, the gel card is brought to a station for capturing images, which here comprises a camera connected to a user interface, for displaying images of the reaction results. In the example, the interpretation of the reaction results is carried out automatically, notably by means of a suitable piece of software.

In other examples, the analysis of the results is directly achieved by the operator who views them either with a naked eye or on the display unit of the user interface. The operator may for example detect the absence or the presence of a colored sediment at the bottom of the card well, and infer therefrom the positivity or negativity of the reaction.

The medical analysis machine 100 illustrated in FIG. 1 comprises a chassis 10 supporting, for achieving the different aforementioned operations, a plurality of storage and/or analysis members listed below:

an inlet and outlet magazine 12 for gel card baskets 14 each supporting a plurality of gel cards (for example 12) 16, for reagent flasks 36 and for diluent containers 28, each diluent container 28 here comprising an injected part 30 providing with a plurality of covered cavities 32 filled with diluent (in the illustrated example, only gel card baskets appear at the inlet magazine; the flasks of reagents and the containers with diluent are however visible in other locations of the machine, as described hereafter);

an incubator 18;

an area for preparing assemblies of gel cards to be pipetted 19 (also called "batches");

an area for storing reusable gel cards (not shown), i.e. gel cards for which only some wells have been used;

an area for loading/unloading supports of sample tubes 20, each support of sample tubes 22 being provided with cylindrical cavities 24 adapted for receiving the sample tubes 26;

an area 34 for pipetting the reagent flasks 36;

a pipetting robot 38, moveable here along three degrees of freedom (in the example three orthogonal translational axes, including the vertical axis along which moves the pipetting needle), between an area 40 for pipetting sample tubes 26 and diluent containers 28, an area 42 for pipetting gel cards 16 and the area 34 for pipetting the reagent flasks 36;

a gel card centrifuge 44;

a station for capturing images and for control 48 (hereafter control station), comprising a camera 50 connected to a user interface (not shown); and a container or garbage bin 52 for collecting objects such as gel cards 16, sample tubes 22 and reagent flasks 36, after use (for the sake of clarity in FIG. 1, the collecting container 52 is not illustrated to scale).

The analysis machine further comprises a robot 70 substantially located at the center of the machine 100, surrounded by the whole of the aforementioned elements, and provided with a poly-articulated arm 60 described in more detail below.

Figure 2:
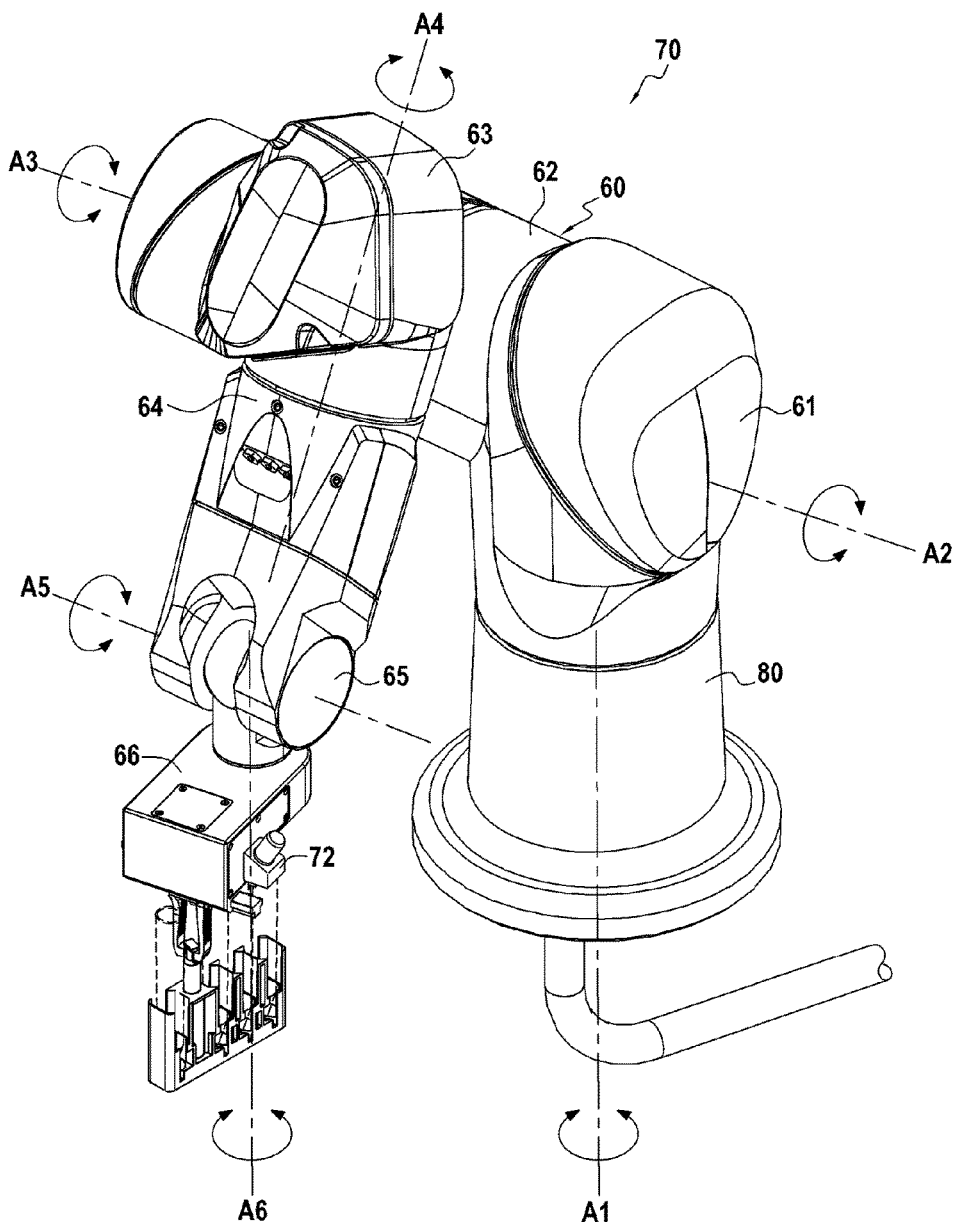
FIGS. 2 and 3 are respectively perspective and front views of the poly-articulated robot of FIG. 1.

In the example, illustrated in more detail in FIG. 2, the arm 60 of the robot 70 comprises a first arm segment 61 extending from a horizontal base 80 attached to the chassis 10 of the machine 100. The first arm segment 61 is substantially located in the center of the machine 100, and pivotally mounted with respect to the base 80 around a first substantially vertical axis A1.

Figure 3:
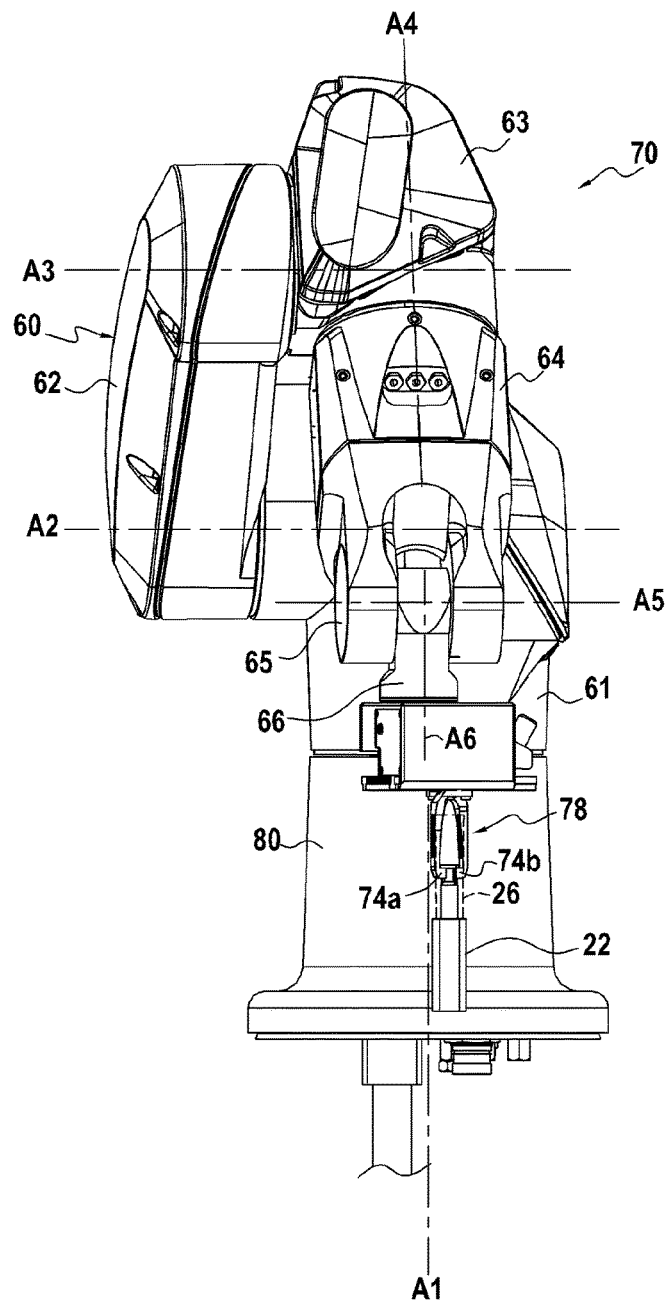
Figure 4:
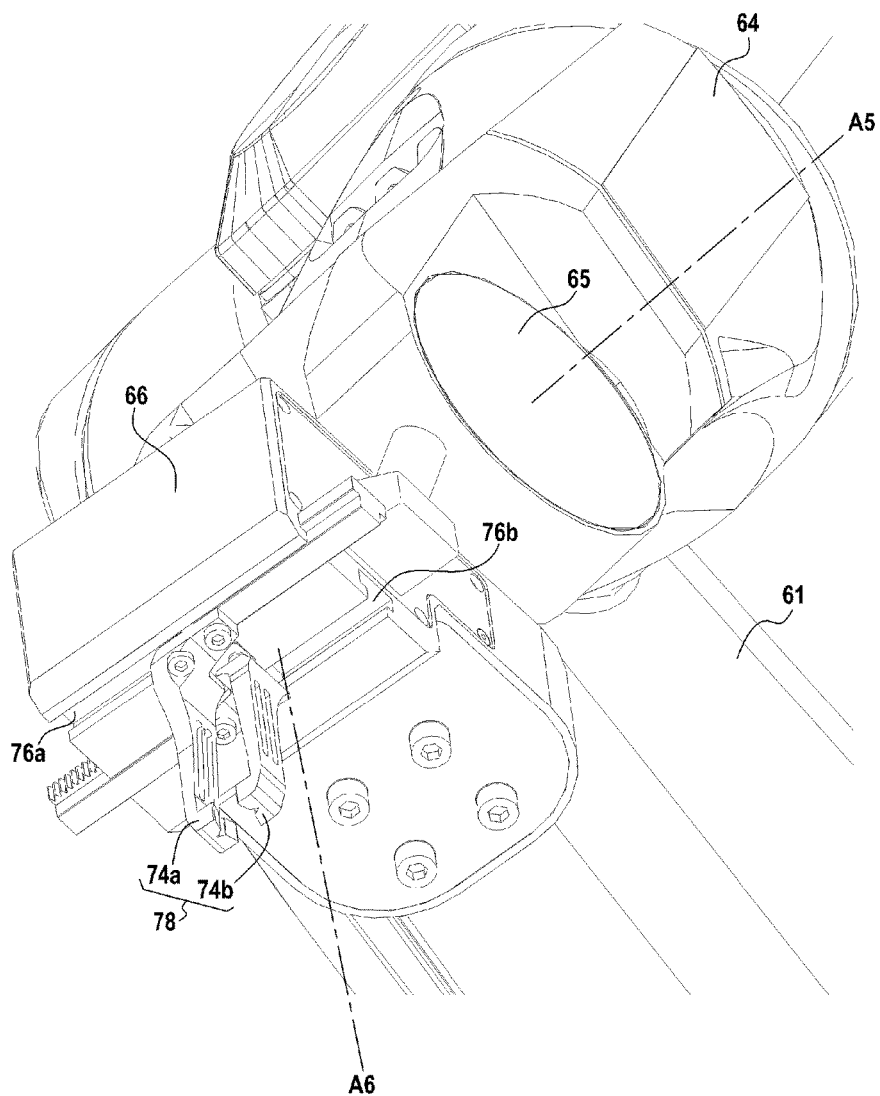
FIG. 4 shows in more detail the terminal member of the poly-articulated robot of FIG. 1.

A second arm segment 62 of the machine, better visible in FIG. 3, is connected to the end of the first arm segment 61 opposite to the base 80 of the machine 100, and articulated relatively to the first arm segment around a second axis A2 perpendicular to the first axis A1.

A third arm segment 63 is connected to the end of the second arm segment 62 opposite to the first arm segment 61, and articulated relatively to the second arm segment 62 around a third axis A3 parallel to A2.

A fourth arm segment 64 is connected to the third arm segment 63 while being pivotally mounted relatively to the latter around a fourth axis A4 perpendicular to the third axis A3.

A fifth arm segment 65 is connected to the fourth arm segment 64 while being pivotally mounted relatively to the latter around a fifth axis A5 perpendicular to the fourth axis A4.

Finally, the arm 60 is terminated by a sixth arm or terminal member segment 66 connected to the end of the fifth arm 65 which is opposite to the fourth arm 64. The sixth arm 66 is pivotally mounted relatively to the fifth arm 65 around a sixth axis A6 perpendicular to the fifth axis A5, and parallel to A2 and A3.

By the six axes of rotation (or pivot type joints) of the arm 60, the terminal member 66 may attain all the workstations distributed over 360° around it, at different heights and along different orientations.

It will be noted that according to an alternative embodiment of the invention, the poly-articulated robot may comprise more than six axes of rotation.

In FIG. 2, the terminal member 66 includes a piezoelectric sensing device 72.

During the manufacturing of the machine or during maintenance operations, and by means of the six axes of rotation of the robot 70, the sensor 72 will sense the different workstations and store in memory the actual coordinates in space of all the elements forming the machine 100. The robot 70 is thus aware of the whole of the positions and orientations of the elements and has an accurate image of the machine. The geometrical defects due to building inaccuracies therefore do not have any impact on the final operation of the machine.

At its lower end, the terminal member 66 further includes two substantially L-shaped jaws 74a, 74b, facing each other, slidably mounted along two slides 76a, 76b directed perpendicularly to the aforementioned axis A6 and parallel with each other. The jaws 74a, 74b form a grasping or clamping member 78 which opens when they are moved apart from each other and closed when they are brought closer to each other.

Preferably, the analysis method according to the invention comprises a step during which the robot 70 displaces the various objects (gel cards 16, reagent flask 36, diluent container 28, etc.) participating in the course of the analytical procedure described above among the different workstations of the machine (control station, loading/unloading areas, pipetting area, garbage bin, etc) by means of its claw 78.

Preferably, the analysis method according to the invention comprises a step during which the poly-articulated robot 70 grasps and shakes an object, for example a reagent flask 36, with its claw 78 in order to resuspend or mix the liquid which is contained therein.

Preferably, the analysis method according to the invention comprises a step during which the robot 70 returns a gel card 16 at the control station 48, by having it pivot by an angle of 180°, so as to allow the shooting of an image on each face.

The analysis method according to the invention may further comprise a step during which the poly-articulated robot actuates an element of the medical analysis machine, for example it displaces the hatch for opening/closing the centrifuge 44, displaces the inlet and outlet magazine 12, in order to make it accessible or inaccessible to the user or to make it accessible to the grasping of gel cards 16 by the poly-articulated robot 70, or further displaces the focusing ring of the camera 50 of the control station 48 during an operation for adjusting the sharpness.

Other steps which may occur in the analysis method according to the invention are described below in connection with FIG. 1.

The method may for example comprise a step during which the robot 70 displaces a support 22 of sample tubes 26, filled with erythrocytes of a patient, or with a suspension of such erythrocytes, towards the control station 48 in order to detect the presence of the tubes 26, detect the presence of plugs on the tubes 26, measure the diameter and the height of the tubes 26, determine the shape of the bottom of the tube 26 or further read the identifier of the tubes 26, for example a barcode.

The method may also comprise a step during which the robot 70 transports the tube support 22 from the control station 48 to the loading/unloading area 20 in order to allow the user to correct an anomaly detected on one or several tubes 26 or to the area for pipetting sample tubes 40.

If required, after the pipetting operation, the method may also comprise a step during which the robot 70 displaces the support of sample tubes 22 once again to the control station 48 for reidentifying the tubes 26.

The method may also comprise a step during which the robot 70 transports the tube support 22 directly from the pipetting area 40 to the loading/unloading area 20 in order to again make the treated sample tubes 26 available to the user.

When the erythrocytes contained in the sample tubes 26 need to be suspended in a diluent, the method may comprise a step during which the robot 70 transports a diluent container 28 initially placed by the user in the inlet magazine 12, to the control station 48 in order to read its identifier. It may then transport it towards the pipetting area 40, or, if required, return it to the magazine 12 in order to allow the user to correct an anomaly (for example when the container 28 is out of date).

The method may further comprise, after the pipetting operation, a step during which the robot 70 displaces the diluent container 28 to the magazine 12 in order to make it again available to the user, to the collecting garbage bin 52 for removing it; or further to the control station 48 for its re-identification if necessary.

The analysis method according to the invention may also comprise a step during which the robot 70 transports a reactive flask 36 which for example depending on the case contains the plasma test or a serum test.

The reagent flask 36 may for example be displaced towards the control station 48 in order to detect the presence of the flask 36 or of a plug on the flask, measure the height of the flask 36, or further read its identifier. The flask 36 may also be displaced towards the pipetting area or towards the inlet and outlet magazine 12 in order to allow the user to correct an anomaly detected on a flask 36 (for example, when a flask has not been opened). From the pipetting area, it may be displaced towards the collecting garbage bin 52 in order to be removed if it is empty or towards the control station 48 so as to be re-identified, in the opposite case.

The analysis method according to the invention may further comprise a step during which the robot 70 transports a gel card 16 initially containing one of the baskets 14 loaded in the inlet magazine 12.

The gel card 16 comprises a body 16a, notably in plastic, extending along a longitudinal direction L, and in which are formed reaction wells 17, for example six wells. These wells 17 have apertures opening into an upper wall 16b of said gel card 16, said apertures being initially obturated with a lid 19 extending along the longitudinal direction L. In the example, the lid 19 is a thin strip sealed to the upper wall 16b of the gel card 16.

Each well 17 of the gel card 16 moreover contains a gel being used for interpreting the results having occurred in the well.

In the illustrated example, each well 17 is formed with an upper cavity 17a of a substantially cylindrical shape connected to a lower cavity 17b with also a substantially cylindrical shape via a frusto-conical intermediate cavity. The upper cavity 17a has a diameter substantially greater than that of the lower cavity 17b, the lower and upper cavities being coaxial.

In a first phase, the gel card 16 may be displaced towards the control station 48 in order to read its identifier or detect the condition of the gel.

It may also be transported from the control station 48 as far as the magazine 12 or as far as the collecting garbage bin 52, for example when the card 16 has been identified as having expired.

The gel card 16 may be displaced towards the area for pipetting a gel card 42. It may also be displaced from the pipetting area 42 towards the control station 48 in order to control the total level of the dispensed liquid, from the control station 48 to the incubator 18, from the incubator 18 to the control station 48, from the control station 48 to the centrifuge 44 for centrifuging it, from the centrifuge 44 to the control station 48 in order to achieve capture of an image of the card 16, from the control station 48 to the internal magazine (not shown) for storing the cards to be re-read manually, from the internal magazine (not shown) to the outlet magazine of gel cards 18 in order to again make available to the user the cards 16 to be re-read manually, from the control station 48 to an area of reuseable cards for forming a supply of reuseable cards for future analysis not requiring a complete gel card, from the reuseable card area to the area for preparing blocks for preparing gel cards in order to form batches of gel cards to be pipetted, from the reuseable card area to the centrifuge in order to balance a centrifuge before its launching, from the reuseable card area to the collecting garbage bin 52 in order to remove expired cards 16 or to free locations in the reuseable card area.

The analysis method according to the invention may also comprise a step during which the robot 70 transports empty baskets 14 initially loaded with gel cards 16, from the inlet magazine 12 to the collecting garbage bin 52 in order to remove the empty baskets 14 which cannot be used in the outlet magazine 12.

The invention claimed is:

1. A medical analysis method using a medical analysis machine provided with a poly-articulated robot comprising joints defining at least six axes of rotation and adapted for displacing and/or orienting a terminal member according to six degrees of freedom, the terminal member bearing a grasping member adapted for grasping a container, said medical analysis method comprising at least the succession of the following steps:
    providing a container filled beforehand with a sample to be treated stemming from a human being or an animal, said sample is one of a type comprising a liquid, biological tissue, or organ tissue from a human being or an animal, said container being a gel card including a body in which are formed several adjacent reaction wells positioned along a single row, the wells containing a gel and being initially obturated with a lid, the grasping member of the poly-articulated robot being configured to grasp and displace such a gel card,
    transferring said container, by means of the poly-articulated robot moving at a first speed, to at least one treatment station of the medical analysis machine,
    treating the sample in the treatment station while maintaining the sample within the container, and
    transferring the container, by means of the poly-articulated robot moving at a second speed, to a station for capturing images of the treated sample and determine the type of sample in said container, wherein the first speed and the second speed are controlled based on the type of the sample disposed within the container so as to avoid overflow or stirring of the liquid, and determining, automatically with the medical analysis machine and based at least in part on the images, whether treating the sample resulted in a positive reaction within the container or a negative reaction within the container,
    the method further comprising a prior parameterization step including:
    sensing respective coordinates of different stations of the medical analysis machine using a piezo-electric sensing device of the terminal member, and wherein the coordinates are stored in a memory associated with the medical analysis machine, and
        defining, based at least in part on the respective coordinates, first and second areas of the medical analysis machine, wherein
        the first areas comprise areas, including the at least one treatment station and the station for capturing images, where the poly-articulated robot is allowed to move, and
        the second areas comprise areas different from the first areas, the at least one treatment station, and the station for capturing images, the poly-articulated robot being prohibited from passing horizontally over the second areas of the medical analysis machine.

2. The medical analysis method according to claim 1, wherein the step for treating the sample comprises the introduction into the container of a reagent adapted to react with the sample to be treated.

3. The medical analysis method according to claim 1, comprising a prior step during which the sample is extracted from a storage receptacle and introduced into the container by means of the poly-articulated robot.

4. The method according to claim 1, wherein the poly-articulated robot is secured to a fixed base and exclusively comprises rotoidal joints.

5. The analysis method according to claim 1, wherein the medical analysis performed belongs to any of the fields from among immune-hematology, virology, microbiology, bacteriology, mycology, parasitology, quality control for an in vitro diagnostic laboratory, detection of auto-immune diseases, monitoring diabetes, detecting genetic diseases, toxicology and the monitoring of a physiological or pathological condition, subsequent to therapeutic treatment.

6. The method according to claim 1, wherein the container is brought to the station for capturing images of the treatment results by means of the poly-articulated robot.

7. The method according to claim 1, during the transfer step, the container is brought by means of the poly-articulated robot to a control station of the medical analysis machine.

8. The method according to claim 7, wherein the station for capturing images of the treatment results and the control station are a single and same station.

9. The medical analysis method according to claim 1, wherein:
    the container filled beforehand with the sample to be treated by means of the poly-articulated robot is brought to an area for pipetting said container in order to introduce a reagent therein,
    the reagent is introduced into the container,
    the container is brought to an incubator by means of the poly-articulated robot,
    the container is incubated,
    the container is brought by means of the poly-articulated robot from the incubator to a centrifuge,
    the container is centrifuged,
    the container is transferred to the station for capturing images.

10. The method according to claim 9, wherein, before the step of introducing the reagent into the container, a reagent flask is turned upside down and/or shaken by means of the poly-articulated robot, the reagent being thereby resuspended.

11. The analysis method according to claims 9, wherein before the centrifugation step, the container is brought, by means of the poly-articulated robot, to a control station where the container is viewed in order to check the air gaps.

12. The method according to claim 1, wherein the container is brought, by means of the poly-articulated robot, to a collecting container intended for recovering the waste.

13. The method according to claim 1, wherein the machine comprises a plurality of treatment stations which are distributed over 360° around the poly-articulated robot.

* * * * *